(12) United States Patent
Heser et al.

(10) Patent No.: US 12,064,298 B2
(45) Date of Patent: Aug. 20, 2024

(54) MEDICAL DEVICE SUPPORT SYSTEM INCLUDING ROTATIONAL CONTROL MECHANISM

(71) Applicant: American Sterilizer Company, Mentor, OH (US)

(72) Inventors: Michael Joseph Heser, Willoughby, OH (US); Jerime Josef Pichler, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 430 days.

(21) Appl. No.: 17/554,011

(22) Filed: Dec. 17, 2021

(65) Prior Publication Data
US 2022/0211463 A1  Jul. 7, 2022

Related U.S. Application Data

(60) Provisional application No. 63/134,254, filed on Jan. 6, 2021, provisional application No. 63/134,263, filed
(Continued)

(51) Int. Cl.
*A61B 90/50* (2016.01)
*A61B 90/00* (2016.01)
(Continued)

(52) U.S. Cl.
CPC .............. *A61B 90/50* (2016.02); *A61B 90/03* (2016.02); *A61B 90/35* (2016.02); *F21V 21/28* (2013.01);
(Continued)

(58) Field of Classification Search
CPC ... A61B 90/00; A61B 90/03; A61B 2090/035; A61B 90/35; A61B 34/30; A61B 34/70;
(Continued)

(56) References Cited

U.S. PATENT DOCUMENTS 3,240,925 A   3/1966  Kaschke et al.
6,471,363 B2  10/2002 Howell et al.
(Continued)

FOREIGN PATENT DOCUMENTS

EP   3537023 A1 *  9/2019  ........... F16M 11/041
WO   2020/159616 A1  8/2020

OTHER PUBLICATIONS

International Search Report and Written Opinion for corresponding International No. PCT/US2021/063972, completion date Mar. 14, 2022.

*Primary Examiner* — Tan-Uyen T Ho
*Assistant Examiner* — Bridget E. Rabaglia
(74) *Attorney, Agent, or Firm* — Renner, Otto, Boisselle & Sklar, LLP

(57) ABSTRACT

A medical device support system including a shaft, extension arm, and floating stop. A guide channel member is fixed to the shaft and includes an elongated cavity that defines first and second contact faces at its opposite ends. A hub of the extension arm is pivotably mounted for a range of at least 360 degrees rotation about a rotation axis of the shaft. The at least 360 degrees rotation range is based on a compound of a first rotation range and a second rotation range. The first rotation range is defined by a fixed stop of the hub configured to move between first and second contact faces of a radially outer portion of the floating stop. The second rotation range is defined by a radially inner portion of the floating stop configured to move between the first and second contact faces of the elongated cavity of the guide channel member.

20 Claims, 11 Drawing Sheets

Related U.S. Application Data on Jan. 6, 2021, provisional application No. 63/134,248, filed on Jan. 6, 2021.

(51) Int. Cl.
  *A61B 90/35* (2016.01)
  *F21V 21/28* (2006.01)

(52) U.S. Cl.
  CPC ... *A61B 2090/035* (2016.02); *A61B 2090/508* (2016.02)

(58) Field of Classification Search
  CPC .............. A61B 34/72; A61B 2034/301; A61B 2034/302; A61B 2034/303; A61B 2034/304; A61B 2017/00477; A61B 34/35; F16M 11/2014; F16M 11/08; F16M 13/02; F16M 13/027
  USPC .......................................... 606/130; 248/592
  See application file for complete search history.

(56) References Cited

U.S. PATENT DOCUMENTS

| | | |
|---|---|---|
| 8,070,331 B2 | 12/2011 | Gull et al. |
| 8,757,345 B2 | 6/2014 | Blank et al. |
| 8,899,834 B2 | 12/2014 | Barker et al. |
| 9,239,127 B2 | 1/2016 | Kronung |
| 9,945,498 B2 | 4/2018 | Timoszyk et al. |
| 2020/0030056 A1 | 1/2020 | Bellows et al. |
| 2020/0306006 A1 | 10/2020 | Bellows et al. |

\* cited by examiner

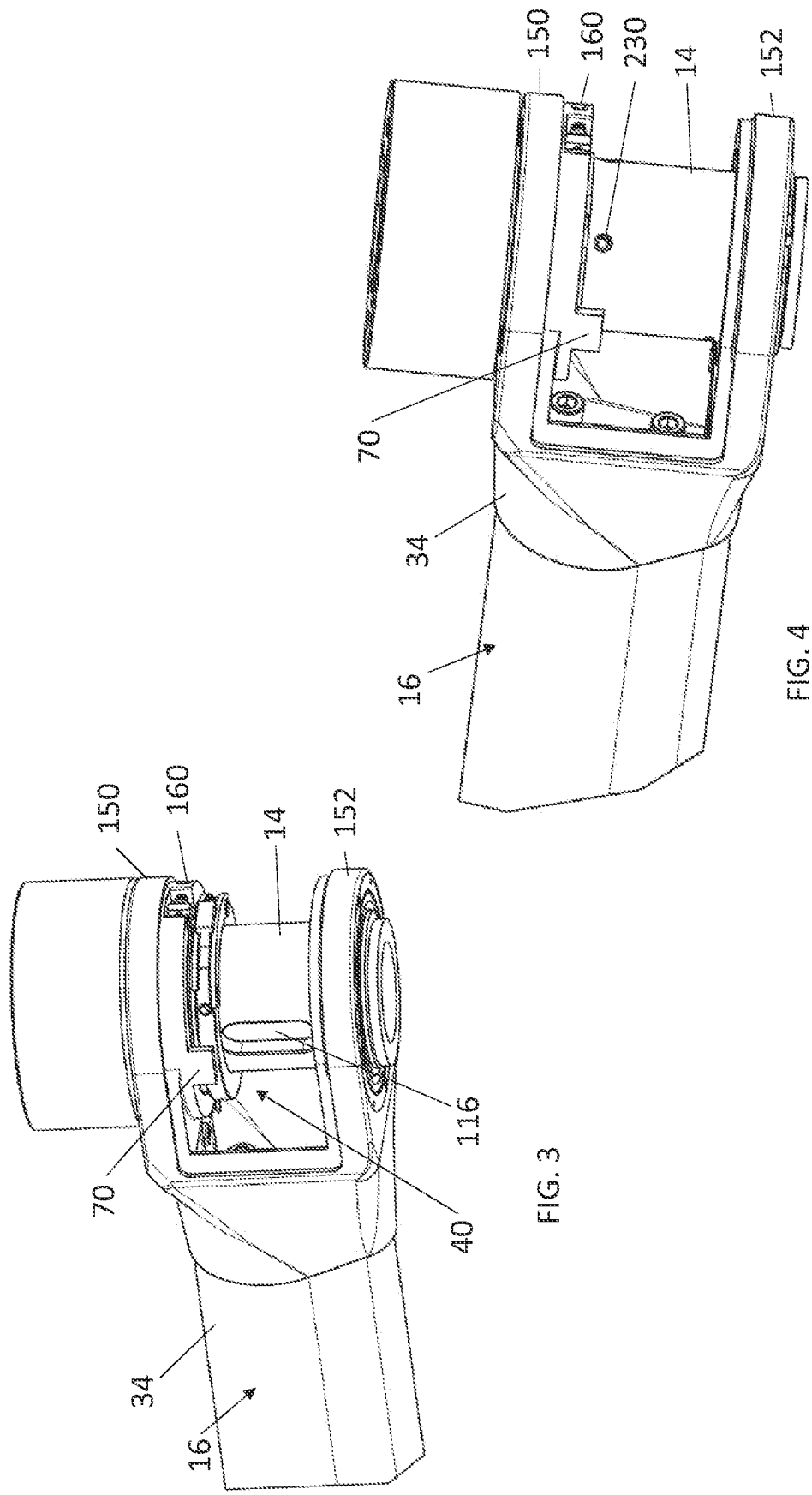

FIG. 8 CCW

MEDICAL DEVICE SUPPORT SYSTEM INCLUDING ROTATIONAL CONTROL MECHANISM

RELATED APPLICATIONS

This application claims the benefit of U.S. Provisional Application No. 63/134,248, filed Jan. 6, 2021, U.S. Provisional Application No. 63/134,254, filed Jan. 6, 2021, U.S. Provisional Application No. 63/134,263, filed Jan. 6, 2021, which are hereby incorporated herein by reference in their entireties.

FIELD OF INVENTION

This application relates generally to a rotational control mechanism for a medical device suspension system or carry system for use in, for example, a hospital examination room, a clinic, a surgery room or an emergency room, and more particularly to a rotational control mechanism that simplifies rotational control of an extension arm about a shaft of the medical device support system and provides at least 360° (360 degrees) rotation of the extension arm about the shaft.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The systems typically include a shaft or support spindle that is suspended from the ceiling or mounted to a wall or stand, and one or more generally horizontal extension arms mounted for rotational movement about the shaft. Each extension arm typically has a hub at its proximal end mounted to the shaft for pivotable movement about the shaft, and a support at its distal end for supporting a medical device. The extension arm can be rotatably adjusted about the shaft to a desired angular position to provide appropriate access to medical devices and components associated with the arm.

It is desirable to limit the rotation of the extension arm about the shaft for example to prevent collision of medical devices at the distal ends of the arms, or to prevent undue strain on electrical or communication lines passing through the shaft and the extension arm. In most current support systems, the extension arm is equipped with a fixed feature in the hub that contacts a fixed feature on the shaft that prevents further rotation.

For rotational control mechanisms in some medical device suspension systems or carry systems, there remain various shortcomings, drawbacks, and disadvantages relative to certain applications. For example, in some systems the rotational control mechanism limits rotation of the extension arm to below 360° (360 degrees), which may limit options for some installations. Other rotational control mechanisms require multiple stacked components, which increase the volumetric footprint of the mechanisms and complicates their integration into the hub of the extension arm.

Accordingly, there remains a need for further contributions in this area of technology.

SUMMARY OF INVENTION

The application relates to a rotational control mechanism for a medical device support system, in which the rotational control mechanism enables at least 360° (360 degrees) rotation of the extension arm about the shaft, and also embodies fewer components and a smaller volumetric footprint than heretofore attained, thus simplifying and adding efficiency to the factory assembly and field service of the medical device support system.

According to one aspect of the invention, a medical device support system includes a shaft, an extension arm, a guide channel member, and a floating stop. The extension arm may have a support for a medical device and a hub at its proximal end mounted to the shaft for pivotable movement about a rotation axis of the shaft. The guide channel member may be fixed to the shaft. The guide channel member may include an elongated cavity that defines first and second contact faces at opposite ends of the cavity. The floating stop may be movable within the elongated cavity of the guide channel member and movable relative to the hub. The hub may be pivotably mounted for a range of at least 360° (360 degrees) rotation about the rotation axis, wherein the at least 360° (360 degrees) rotation range is based on a compound of a first rotation range and a second rotation range, wherein the first rotation range is defined by a fixed stop of the hub configured to move between first and second contact faces of a radially outer portion of the floating stop, wherein the second rotation range is defined by a radially inner portion of the floating stop configured to move between the first and second contact faces of the elongated cavity of the guide channel member.

Embodiments of the invention may include one or more of the following additional features separately or in combination.

The guide channel member may include a rotation boundary member that is fixed to the shaft, the rotation boundary member defining as boundaries the first and second contact faces at opposite ends of the cavity.

The rotation boundary member may include a ring shape structure and the ring shape structure may be fixed to the shaft.

The elongated cavity may have an arc shape.

The guide channel member may include a lower guide wall for axially supporting the floating stop.

The guide channel member may include an arc shape track and the floating stop may include an arc shape groove, wherein the arc shape groove slidably receives the arc shape track to angularly guide the floating stop within the elongated cavity and about the rotation axis.

The floating stop may be configured to prevent rotation of the hub about the rotation axis beyond the at least 360° (360 degrees) rotation range.

The hub may be pivotably mounted for at least 360° (360 degrees) rotation from a first stop to a second stop and vice versa, wherein the first stop limits counterclockwise rotation of the hub about the rotation axis and the second stop limits clockwise rotation of the hub about the rotation axis.

The first stop may include the fixed stop of the hub in engagement with the first contact face of the radially outer portion of the floating stop, and the radially inner portion of the floating stop in engagement with the first contact face of the elongated cavity of the guide channel member.

The second stop may include the fixed stop of the hub in engagement with the second contact face of the radially outer portion of the floating stop, and the radially inner portion of the floating stop in engagement with the second contact face of the elongated cavity of the guide channel member.

The radially outer portion of the floating stop and the radially inner portion of the floating stop may lie in the same plane and the plane may be perpendicular to the rotation axis.

The fixed stop of the hub and the radially inner portion of the floating stop may lie in the same plane and the plane may be perpendicular to the rotation axis.

The radially outer portion of the floating stop may include a tab, and the first and second contact faces of the radially outer portion of the floating stop may be on opposite peripheral sides of the tab.

The radially inner portion of the floating stop may have first and second contact faces on opposite sides thereof, and the second rotation range may be defined by movement of the radially inner portion between a location at which the first contact face of the radially inner portion engages the first contact face of the elongated cavity of the guide channel member and a location at which the second contact face of the radially inner portion engages the second contact face of the elongated cavity of the guide channel member.

The shaft may have an axial hollow and a radial aperture and the ring shape structure may be fixed to the shaft at a position to allow passage of electrical and communication lines through the axial hollow, through the ring shape structure, through the radial aperture, and into a longitudinally extending cavity in the extension arm.

The hub of the extension arm may include upper and lower pivot bearings configured to pivotably engage the hub with the shaft, and a radial opening positioned axially between the upper and lower pivot bearings, and the ring shape structure may be positioned to allow passage of the electrical and communication lines between the upper and lower pivot bearings, through the radial opening of the hub, and into the longitudinally extending cavity in the extension arm.

According to another aspect of the invention, a medical device support system includes a shaft, an extension arm, a guide channel member, and a floating stop. The extension arm may have a support for a medical device and a hub at its proximal end mounted to the shaft for pivotable movement about a rotation axis of the shaft. The guide channel member may be fixed to the shaft. The guide channel member may include an elongated cavity that defines first and second contact faces at opposite ends of the cavity. The floating stop may be movable within the elongated cavity of the guide channel member and movable relative to the hub. The hub may be pivotably mounted for a range of at least 360° (360 degrees) rotation about the rotation axis from a first stop to a second stop and vice versa, wherein the first stop limits counterclockwise rotation of the hub about the rotation axis and the second stop limits clockwise rotation of the hub about the rotation axis, wherein the first stop includes a radially inner portion of the floating stop in engagement with the first contact face of the elongated cavity of the guide channel member, and wherein the second stop includes the radially inner portion of the floating stop in engagement with the second contact face of the elongated cavity of the guide channel member.

Embodiments of the invention may include one or more of the following additional features separately or in combination.

The hub may include a fixed stop movable between first and second contact faces of a radially outer portion of the floating stop.

The first stop may include the fixed stop of the hub in engagement with the first contact face of the radially outer portion of the floating stop, and the second stop may include the fixed stop of the hub in engagement with the second contact face of the radially outer portion of the floating stop.

According to another aspect of the invention, there is provided a method of rotating an extension arm about a shaft of a medical device support system, the extension arm having a support for a medical device and a hub at its proximal end mounted to the shaft for pivotable movement about a rotation axis of the shaft, wherein a guide channel member is fixed to the shaft, wherein the guide channel member includes an elongated cavity that defines first and second contact faces at opposite ends of the cavity, wherein a floating stop is movable within the elongated cavity of the guide channel member and movable relative to the hub, the method including rotating the hub over a range of at least 360° (360 degrees) about the rotation axis, wherein the at least 360° (360 degrees) rotation range is based on a compound of movement over a first rotation range and movement over a second rotation range, wherein movement over the first rotation range includes moving a fixed stop of the hub between first and second contact faces of a radially outer portion of the floating stop, and wherein movement over the second rotation range includes moving a radially inner portion of the floating stop between the first and second contact faces of the elongated cavity of the guide channel member.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 3 is a bottom isometric view of the FIG. 2 shaft and extension arm hub connection, showing a rotation boundary member attached to the shaft.

FIG. 4 is a view similar to the FIG. 3 view but omitting the rotation boundary member on the shaft to show underlying detail.

DETAILED DESCRIPTION

Figure 1:
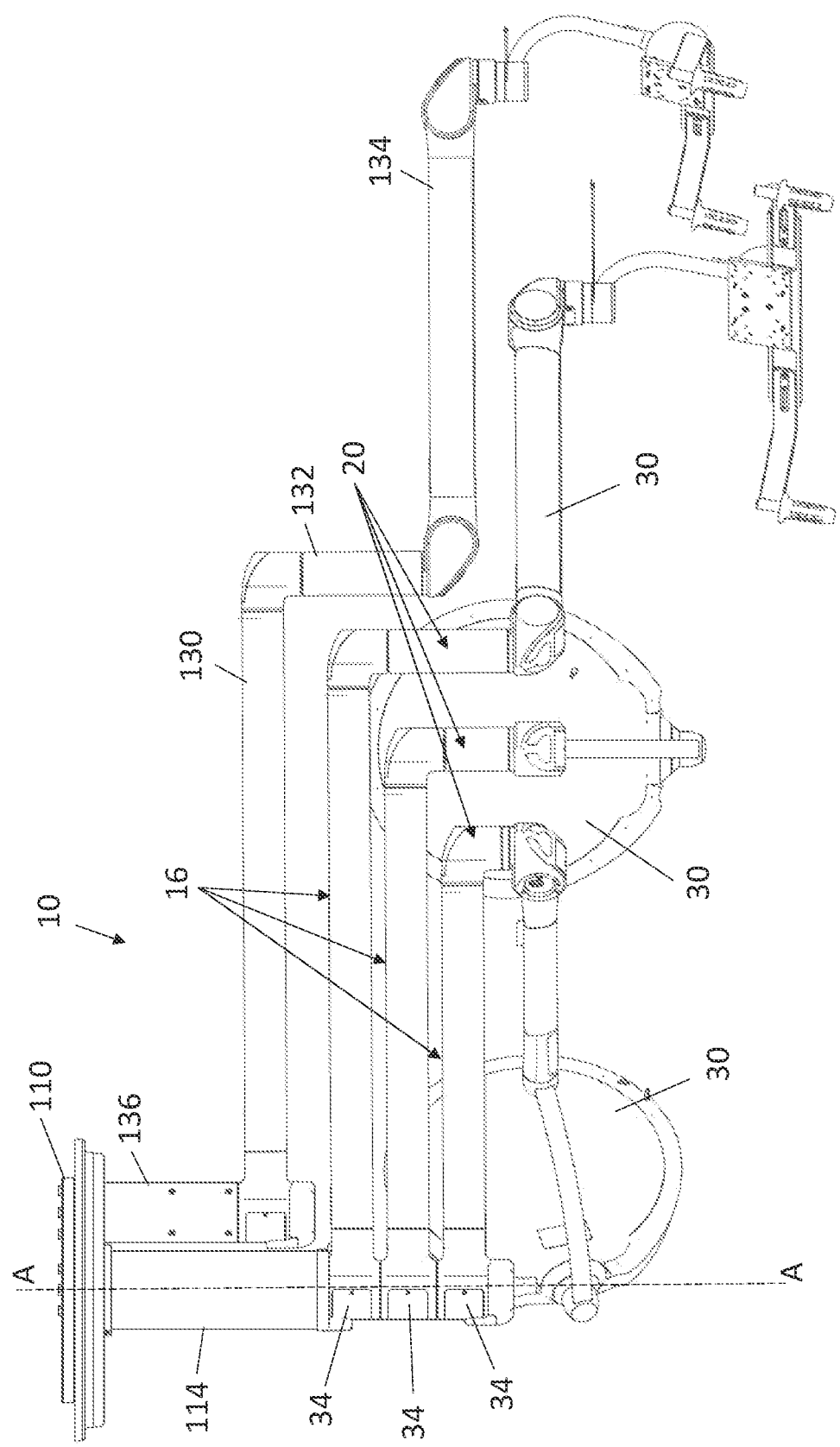
FIG. 1 is a front elevational view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIGS. 1-8 show a medical device support system 10 that includes a shaft 14, at least one extension arm 16 having a support 20 for a medical device 30 and a hub 34 at its proximal end mounted to the shaft 14 for pivotable movement about a rotation axis A-A of the shaft 14, and a rotational control mechanism 40 integrated into the hub 34 for controlling the amount of rotation of the extension arm 16 about the shaft 14. The rotational control mechanism 40 includes a guide channel member 44, a fixed stop 70 connected to a wall of the hub 34, and a floating stop 60 having a radially outer portion 80 and a radially inner portion 90, the radially inner portion 90 being relatively closer to the rotation axis A-A than the radially outer portion 80. The guide channel member 44 in the illustrative embodiment includes a rotation boundary member 46 that is fixed to the shaft 14. The guide channel member 44 includes an elongated cavity 50 that defines first and second contact faces 52, 54 at opposite ends of the cavity 50. The floating stop 60 is movable within the elongated cavity 50 of the guide channel member 44 and movable relative to the hub 34. The hub 34 is pivotably mounted for a range of at least 360° (360 degrees) rotation about the rotation axis A-A, wherein the at least 360° (360 degrees) rotation range is based on a compound of a first rotation range and a second rotation range. The first rotation range is defined by the fixed stop 70 of the hub 34 configured to move between first and second contact faces 82, 84 of the radially outer portion 80 of the floating stop 60. The second rotation range is defined by the radially inner portion 90 of the floating stop 60 configured to move between the first and second contact faces 52, 54 of the elongated cavity 50 of the guide channel member 44.

Figure 2:
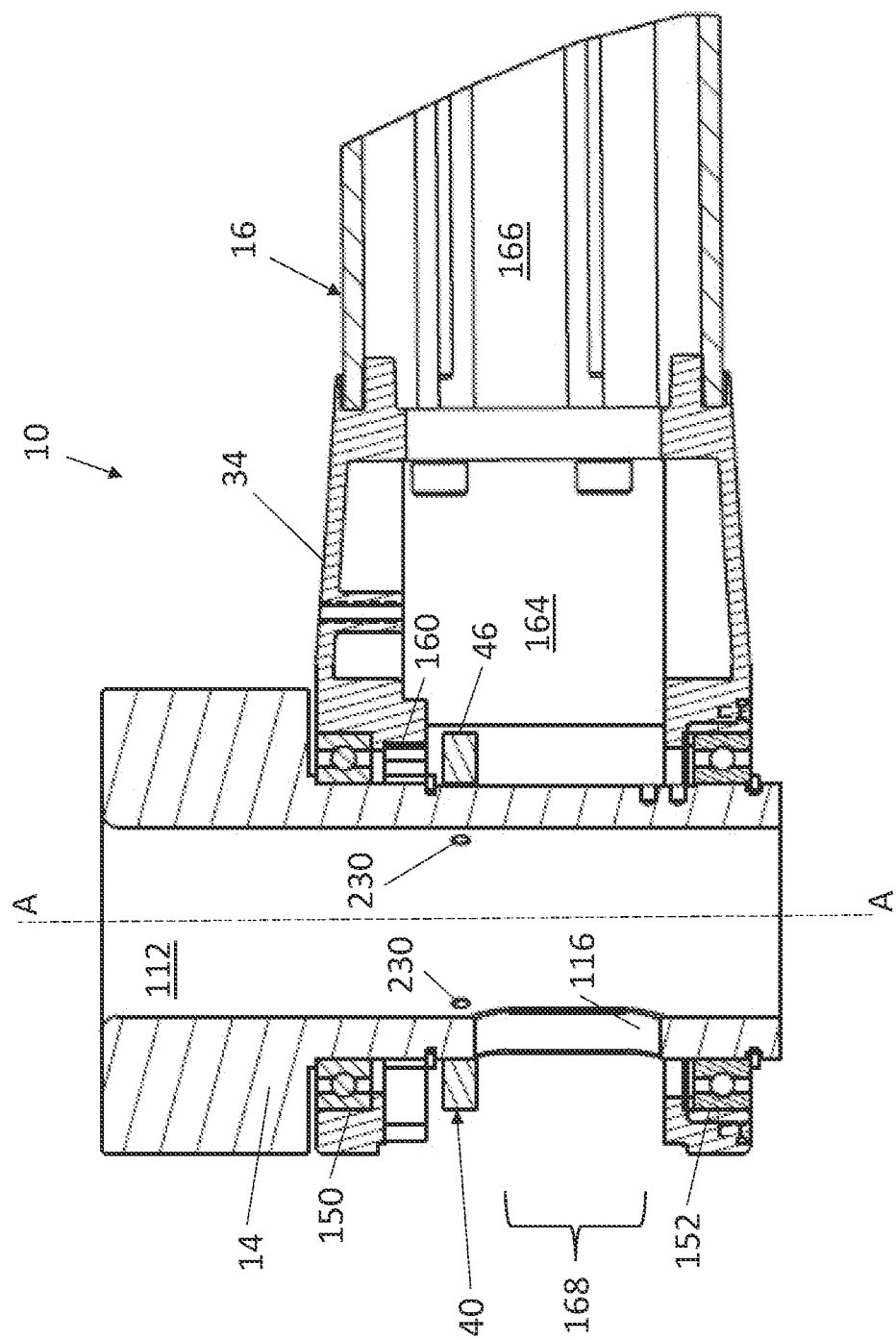
FIG. 2 is a cross section view of a shaft and extension arm hub connection of the FIG. 1 medical device support system, showing a rotational control mechanism in accordance with an embodiment of the invention.
Figure 6:
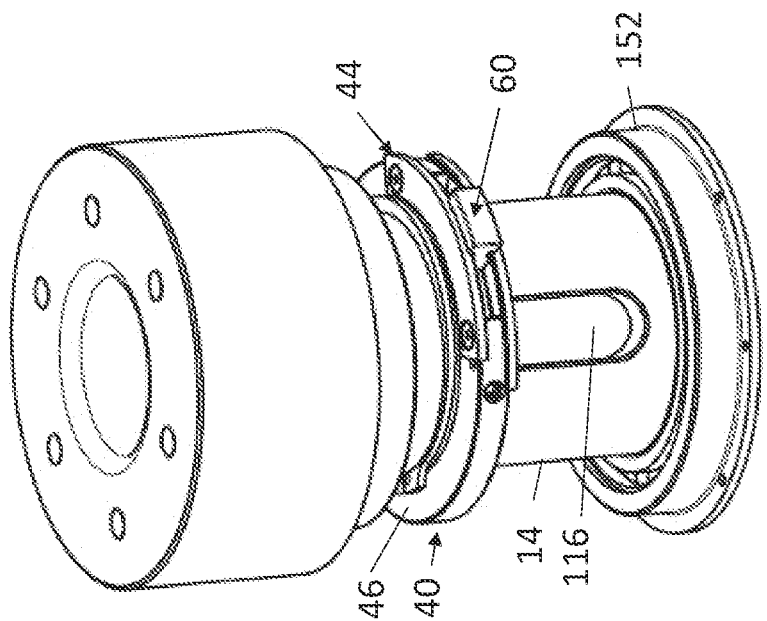
FIG. 6 is a top isometric view similar to the FIG. 4 view but omitting extension hub structure to show underlying detail.
Figure 5:
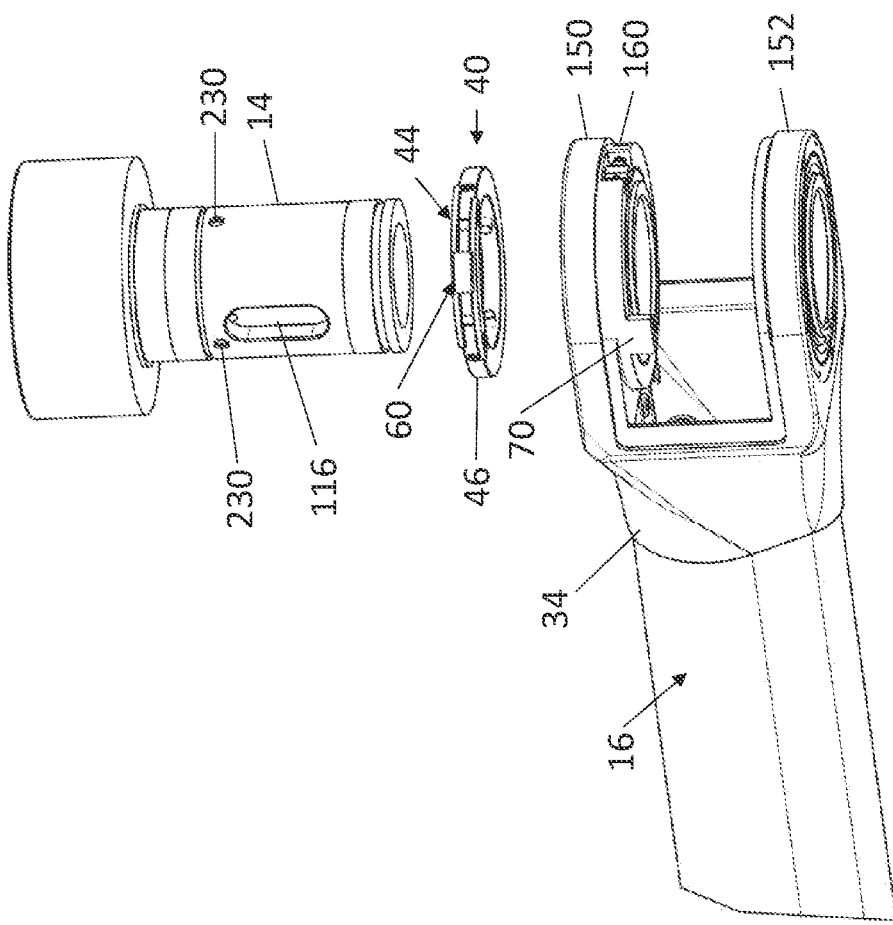
FIG. 5 is an exploded bottom isometric view of the FIG. 2 shaft and extension arm hub connection.

Referring to FIGS. 1 and 2, the illustrative medical device support system 10 is a suspension type carrying support system for use in a hospital examination room, a clinic, a surgery room, an emergency room, among others. The shaft 14 extends along an axis A-A, which also represents the rotation axis A-A of the shaft 14 about which the extension arm 16 pivots. The shaft 14 may be fixed to a ceiling support 110 to remain stationary relative to the ceiling. It will be appreciated, of course, that the medical device support system 10 may have any suitable suspension or carrying structure and that the shaft 14 may be attached to a ceiling as shown, or to a wall, floor, movable cart, or a combination of the foregoing. The shaft 14 of the medical device support system 10 has a cylindrical shape in axial cross section and defines an axial hollow 112 and radial aperture 116 therein, and extends vertically downward from the ceiling support 110. A column section 114 surrounds an upper portion of the shaft 14. The axial hollow 112 and the column section 114 house upper portions of accessory and service lines such as power cables for surgical lights and other power requirements, control wiring for control electronics, optical fibers for data communication, and/or tubing for irrigation, suction, etc. A plurality of extension arms 16, three in the illustrative embodiment, are mounted for rotatable movement to the shaft 14 and extend laterally outward from the shaft 14. In the FIG. 1 embodiment, the extension arms 16 extend horizontally, or perpendicularly, relative to the shaft 14. An additional extension arm 130, support arm 132, and medical device 134 may be pivotably mounted to a separate central shaft 136 radially offset from the central shaft 14.

The hub 34 is located at the proximal end of the extension arm 16. In the illustrative embodiment, to aid in the pivotable movement of the extension arm 16 about the shaft 14, each extension arm hub 34 may include upper and lower bearing mounts 150, 152, shown in FIGS. 2-6, that house respective upper and lower pivot bearings mounted to the shaft 14. Any suitable pivot bearings may be used to enable the relative rotational movement between the extension arm 16 and the shaft 14, including for example ball bearings, sleeve bearings, bushings, rotary joints and/or swivel joints. A brake assembly 160 may be secured in the hub 34 for rotation therewith to selectively increase and decrease a frictional braking force to the shaft 14. In the illustrative embodiment, the brake assembly 160 is positioned below the upper bearing 150 and above the guide channel member 44 or the rotation boundary member 46 of the guide channel member 44. Each hub 34 provides a radial opening 164 positioned axially between the upper and lower pivot bearings 150, 152 for routing accessory and service lines from the axial hollow 112 and/or the upper column section 114 through the radial aperture 116 and to a longitudinally extending cavity 166 of the extension arm 16, and/or vice versa. Each hub 34 is also provided with an access opening 168 to enable access to the shaft 14, the rotational control mechanism 40, the upper and lower pivot bearings 150, 152, the brake assembly 160, accessory and service lines, and/or other components within the hub 34. A suitable brake assembly 160 and access opening 168 for the illustrative embodiment are described in U.S. patent application Ser. Nos. 16/517,703; 16/517,704; 16/517,707; and 16/517,708, which are incorporated by reference for all purposes as if fully set forth herein.

Figure 8:
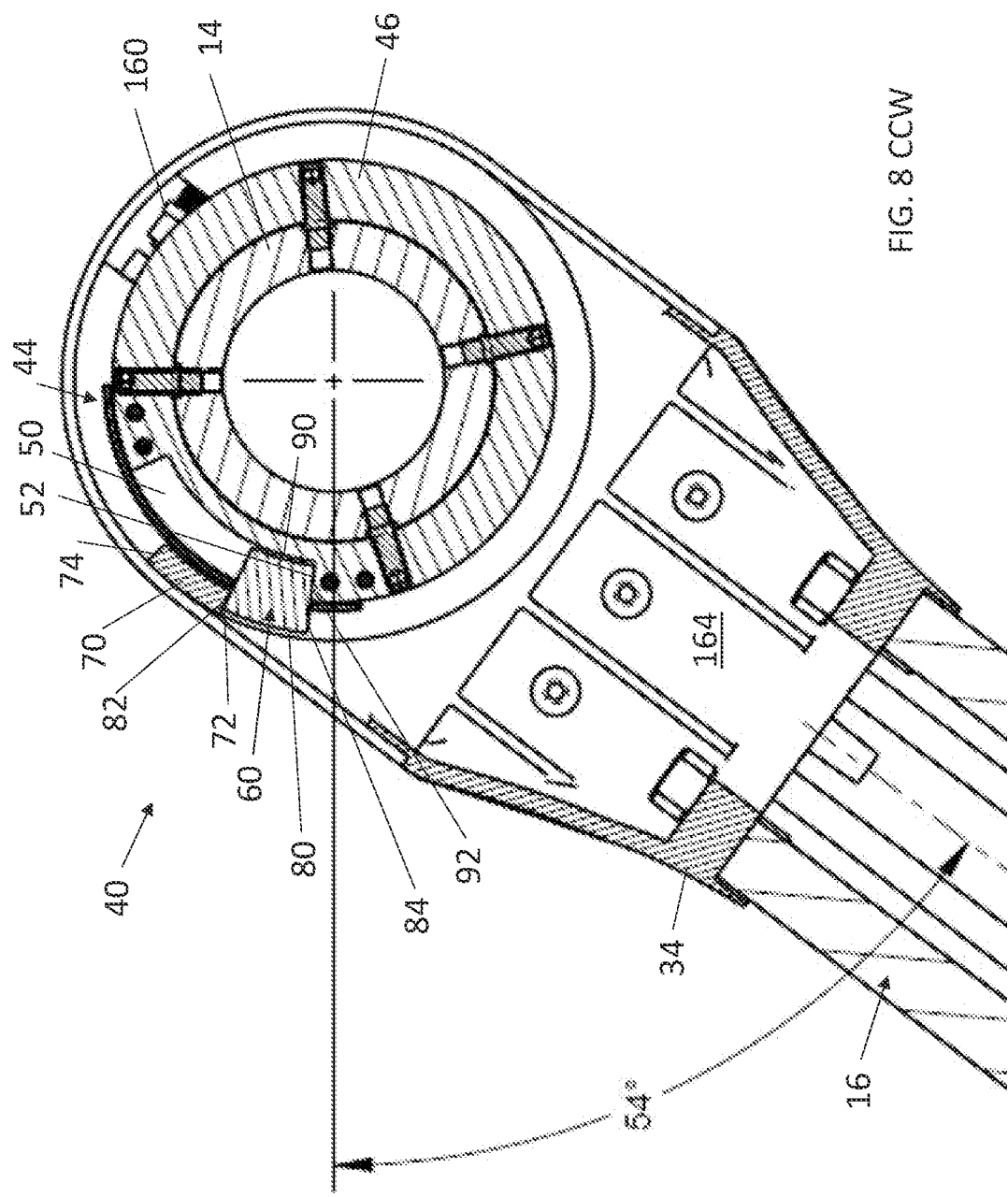
FIG. 8 shows a top cross section view of the rotational control mechanism of the medical device support system of FIG. 1, showing a maximum counterclockwise position of a floating stop of the rotational control mechanism.
Figure 9:
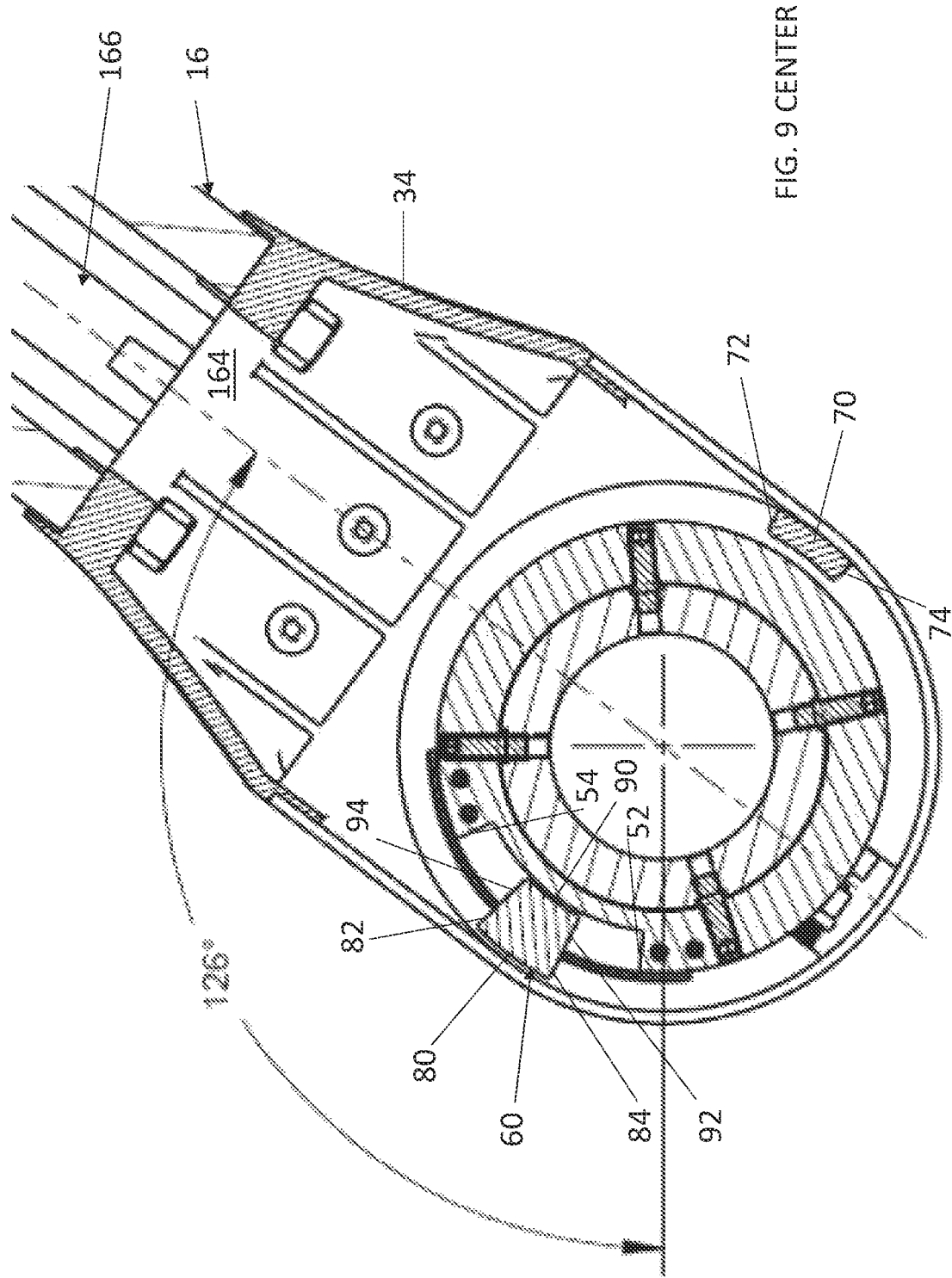
FIG. 9 shows a top cross section view of the rotational control mechanism of the medical device support system of FIG. 1, showing a mid-rotation position of the floating stop of the rotational control mechanism.
Figure 10:
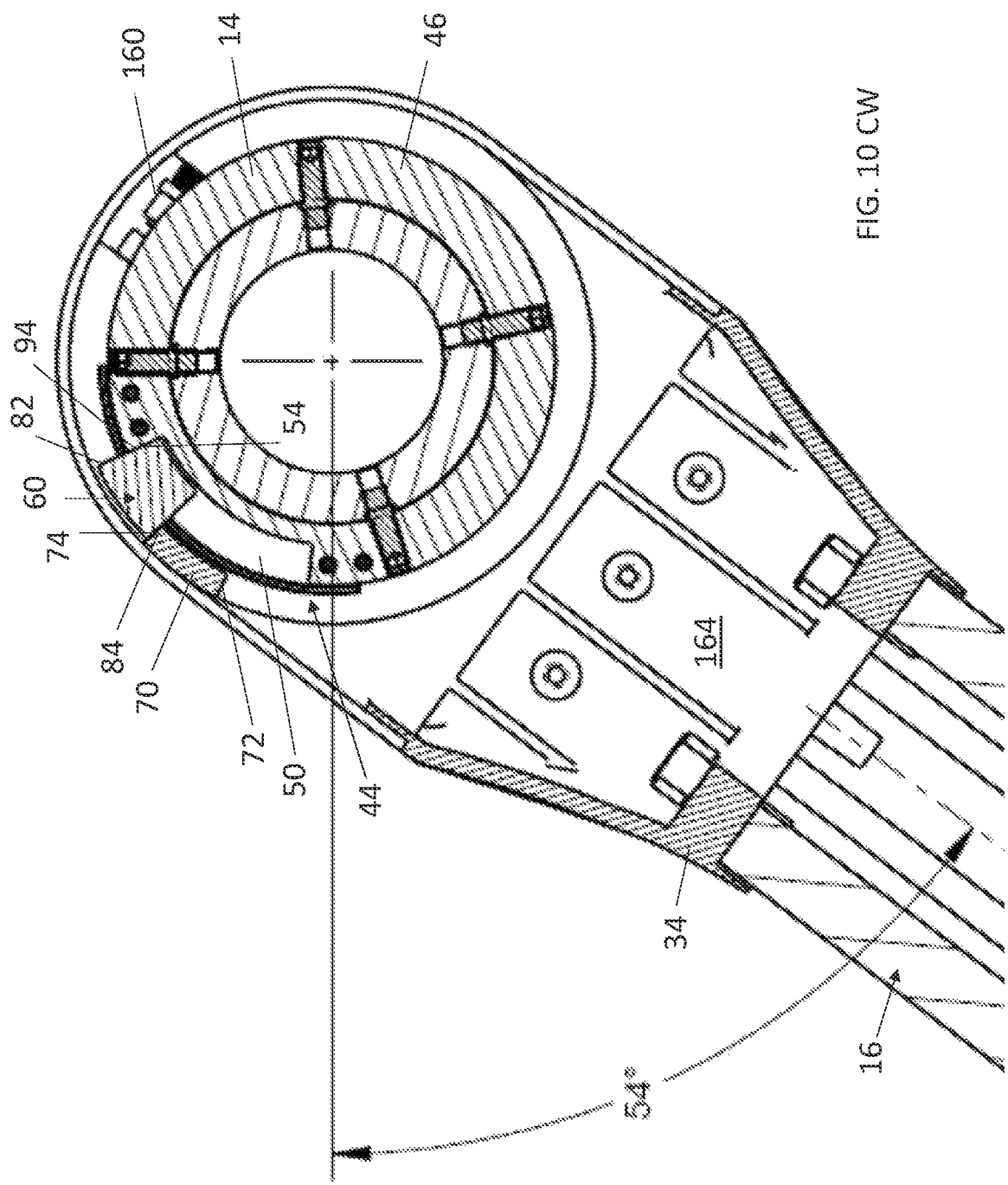
FIG. 10 shows a top cross section view of the rotational control mechanism of the medical device support system of FIG. 1, showing a maximum clockwise position of the floating stop of the rotational control mechanism, where the rotation is at least 360° (360 degrees) rotation from that shown in FIG. 8.

Reference is now made to FIGS. 8-10, which show greater detail of the rotational control mechanism 40. The rotational control mechanism 40 is made up of a combination of components from the hub 34 of the extension arm 16, the guide channel member 44, and the floating stop 60. The hub 34 includes the fixed stop 70. The floating stop 60 includes the radially outer portion 80 and the radially inner portion 90. The guide channel member 44 includes an elongated cavity 50. In FIGS. 8-10, it can be seen that the extension arm 16 and its hub 34 and the fixed stop 70 of the rotational control mechanism 40 are movable relative to the shaft 14. As is also apparent from FIGS. 8-10, the floating stop 60 including its radially outer and inner portions 80, 90, is movable within the elongated cavity 50 of the guide channel mechanism 44 and movable relative to the hub 34 and the fixed stop 70.

Each of the components of the rotational control mechanism 40 provides contact faces, that is, faces for abutting engagement, to control the amount of rotation of the extension arm 16 about the rotation axis A-A of the shaft 14. The fixed stop 70 has first and second contact faces 72, 74 on opposite peripheral ends of the fixed stop 70. The radially outer portion 80 has first and second contact faces 82, 84 on opposite peripheral ends of the radially outer portion 80. The radially inner portion 90 has first and second contact faces 92, 94 on opposite peripheral ends of the radially inner portion 90. The elongated cavity 50 defines first and second contact faces 52, 54 at opposite ends of the cavity 50. In this way, the rotational control mechanism 40 embodies fewer components and a smaller volumetric footprint than heretofore attained and simplifies and adds efficiency to the factory assembly and field service of the medical device support system 10.

The floating stop 60 is configured to prevent rotation of the hub 34 about the rotation axis A-A beyond the at least 360° (360 degrees) rotation range. The hub 34 is pivotably mounted for at least 360° (360 degrees) rotation from a first stop shown in FIG. 8 to a second stop shown in FIG. 10, and vice versa. As shown in FIG. 8, the first stop limits counterclockwise rotation of the hub 34 about the rotation axis A-A. Thus, the first stop defines the most counterclockwise rotation the hub 34 and thus the extension arm 16 obtain about the shaft 14. In FIG. 8, the first stop, or most counterclockwise rotation of the extension arm 16, positions the extension arm 16 at 54° (54 degrees) relative to a horizontal line across the page. As shown in FIG. 10, the second stop limits clockwise rotation of the hub 34 about the rotation axis A-A. Thus, the second stop defines the most clockwise rotation the hub 34 and associated extension arm 16 obtain about the shaft 14. In FIG. 10, the second stop, or most clockwise rotation of the extension arm 16, positions the extension arm 16 at 54° (54 degrees) relative to the horizontal line across the page. As is apparent from FIGS. 8 and 10, the rotation of the extension arm 16 and its hub 34 about the shaft 14 is 360° (360 degrees), which, going from FIG. 8 to FIG. 10, is 360° (360 degrees).

Two abutting engagements form the first or most counterclockwise stop and two abutting engagements form the second or most clockwise stop. Referring to FIG. 8, the first stop includes the fixed stop 70 of the hub 34 in engagement with the first contact face 82 of the radially outer portion 80 of the floating stop 60, and the radially inner portion 90 of the floating stop 60 in engagement with the first contact face 52 of the elongated cavity 50 of the guide channel member 44. Referring to FIG. 10, the second stop includes the fixed stop 70 of the hub 34 in engagement with the second contact face 84 of the radially outer portion 80 of the floating stop 60, and the radially inner portion 90 of the floating stop 60 in engagement with the second contact face 54 of the elongated cavity 50 of the guide channel member 44.

The rotational control mechanism 40 facilitates the at least 360° (360 degrees) rotation range based on a compound of a first rotation range and a second rotation range. As previously noted, the first rotation range is defined by the fixed stop 70 of the hub 34 being configured to move between the first and second contact faces 82, 84 of the radially outer portion 80 of the floating stop 60. In the illustrated embodiment, the angular span between the first and second contact faces 72, 74 of the fixed stop 70 is about 20-degrees. The radially outer portion 80 of the floating stop 60 has an angular span of about 20-degrees between its first and second contact faces 82, 84. With reference to FIG. 8, and assuming that the floating stop 60 remains idle with rotation of the hub 34, the first rotation range is defined by movement of the fixed stop 70 between a location shown in FIG. 8 at which the first contact face 72 of the fixed stop 70 engages the first contact face 82 of the radially outer portion 80 of the floating stop 60 and a location at which the second contact face 74 of the fixed stop 70 engages the second contact face 84 of the radially outer portion 80 of the floating stop 60. In other words, and again with reference to FIG. 8 and assuming the floating stop 60 remains stationary, the first rotation range is defined by the fixed stop 70 moving from the position shown in FIG. 8 where the first contact face 72 abuttingly engages the first contact face 82, to a position where the second contact face 74 abuttingly engages the second contact face 84; that is, in FIG. 8, the fixed stop 70 moves from the first contact face 82 of the radially outer portion 80 (or right side thereof in FIG. 8) clockwise to the second contact face 84 of the radially outer portion 80 (or left side thereof in FIG. 8). In the FIGS. 8-10 embodiment, the first rotation range of the rotational control mechanism 40 is approximately 320° (320 degrees) (360 minus 20 minus 20).

The second rotation range is defined by the radially inner portion 90 of the floating stop 60 being configured to move between the first and second contact faces 52, 54 of the elongated cavity 50 of the guide channel member 44. In the illustrated embodiment, the angular span between the first and second contact faces 52, 54 of the elongated cavity 50 is about 60-degrees. The radially inner portion 90 of the floating stop 60 has an angular span of about 20-degrees between its first and second contact faces 92, 94. With continued reference to FIG. 8, it is assumed that the hub 34 has rotated clockwise the first rotation range, that is, the second contact face 74 of the fixed stop 70 is in abutting engagement with the second contact face 84 of the radially outer portion 80 of the floating stop 60, and thus continued clockwise rotation of the hub 34 causes the hub 34 and floating stop 60 to rotate together clockwise in unison. The second rotation range is defined by movement of the radially inner portion 90 of the floating stop 60 between a location at which the first contact face 92 of the radially inner portion 90 engages the first contact face 52 of the elongated cavity 50 of the guide channel member 44 and a location shown in FIG. 10 at which the second contact face 94 of the radially inner portion 90 engages the second contact face 54 of the elongated cavity 50 of the guide channel member 44. In other words, and again with reference to FIG. 8 and assuming the second contact face 74 is in abutting engagement with the second contact face 84, the second rotation range is defined by the radially inner portion 90 moving from the position shown in FIG. 8 where the first contact face 92 abuttingly engages the first contact face 52, to a position where the second contact face 94 abuttingly engages the second contact face 54; that is, in FIG. 8, the radially inner portion 90 moves from the first contact face 52 of the elongated cavity 50 clockwise to the second contact face 54 of the elongated cavity 50. In the FIGS. 8-10 embodiment, the second rotation range of the rotational control mechanism 40 is approximately 40° (40 degrees) (60 minus 20).

As will be appreciated, in operation the first and second rotation ranges usually will not be completed in serial fashion but rather at least partially in parallel fashion. This is illustrated in FIG. 9, for example, where the hub 34, relative to the FIG. 8 position, has been rotated clockwise about the shaft 14 about 180° (180 degrees) to a position at which the fixed stop 70 has reached 180° (180 degrees) from the radially outer portion 80 of the floating stop 60, that is, the middle of the first rotation range, and the radially inner portion 90 has reached the middle of the elongated cavity 50, that is, the middle of the second rotation range. It will be appreciated that the movement of the fixed stop 70 between the first and second contact faces 82, 84 of the radially outer portion 80, and the movement of the radially inner portion 90 between the first and second contact faces 52, 54 of the elongated cavity 50, will vary depending on the friction between the respective rotating sliding surfaces of the guide channel member 44, the hub 34, and the floating stop 60. Thus, while FIG. 8 shows the start of the first and second rotation ranges, and FIG. 10 shows the completion of the first and second rotation ranges, what occurs between the start and completion of the first and second rotation ranges will depend on the friction between the rotating sliding surfaces.

It will be appreciated that the rotational control mechanism 40 can provide a greater than 360° (360 degrees) rotation range by adjusting any of its components, for the example the width (angular span) of any of the elongated cavity 50, the fixed stop 70, the radially outer portion 80 of the floating stop 60, and/or the radially inner portion 90 of the floating stop 60. As an example, in the case where the fixed stop 70 is 1.0° (1.0 degree) smaller in width in FIGS. 8-10, then in FIG. 8, the first stop, or most counterclockwise rotation of the extension arm 16, positions the extension arm 16 at 55° (55 degrees) relative to a horizontal line across the page, and in FIG. 10, the second stop, or most clockwise rotation of the extension arm 16, positions the extension arm 16 at 54° (54 degrees) relative to the horizontal line across the page. The total rotation of the extension arm 16 and its hub 34 about the shaft 14 is then 361° (361 degrees), where the first rotation range is 321° (321 degrees) (360 minus 19 minus 20) and the second rotation range is 40° (40 degrees) (60 minus 20).

In exemplary embodiments, the angular span between the first and second contact faces 72, 74 (e.g., width of fixed stop 70) may be in a range from about 1-degree to about 60-degrees, even more particularly between 1-degree and 45-degrees, such as about 20-degrees in the illustrated embodiment. In exemplary embodiments, the radially outer portion 80 of the floating stop 60 may have an angular span in a range from about 1-degree to about 60-degrees, even more particularly between 1-degree and 45-degrees, such as about 20-degrees in the illustrated embodiment. In exemplary embodiments, the elongated cavity 50 forms an arcuate segment defined by an angular span between the opposite first and second contact faces 52, 54 that may be in a range from about 1-degree to about 180-degrees, and even more particularly from about 10-degrees to about 90-degrees, such as about 60-degrees in the illustrated embodiment. In exemplary embodiments, the radially inner portion 90 of the floating stop 60 may have an angular span in a range from about 1-degree to about 60-degrees, even more particularly between 1-degree and 45-degrees, such as about 20-degrees in the illustrated embodiment. In exemplary embodiments, the at least 360-degrees range provided by the rotational control mechanism 40 may be in a range from 360-degrees to less than 720-degrees, more particularly from 360-degrees to 540-degrees, and even more particularly from 360-degrees to 450-degrees, such as about 360-degrees in the illustrated embodiment.

Figure 11:
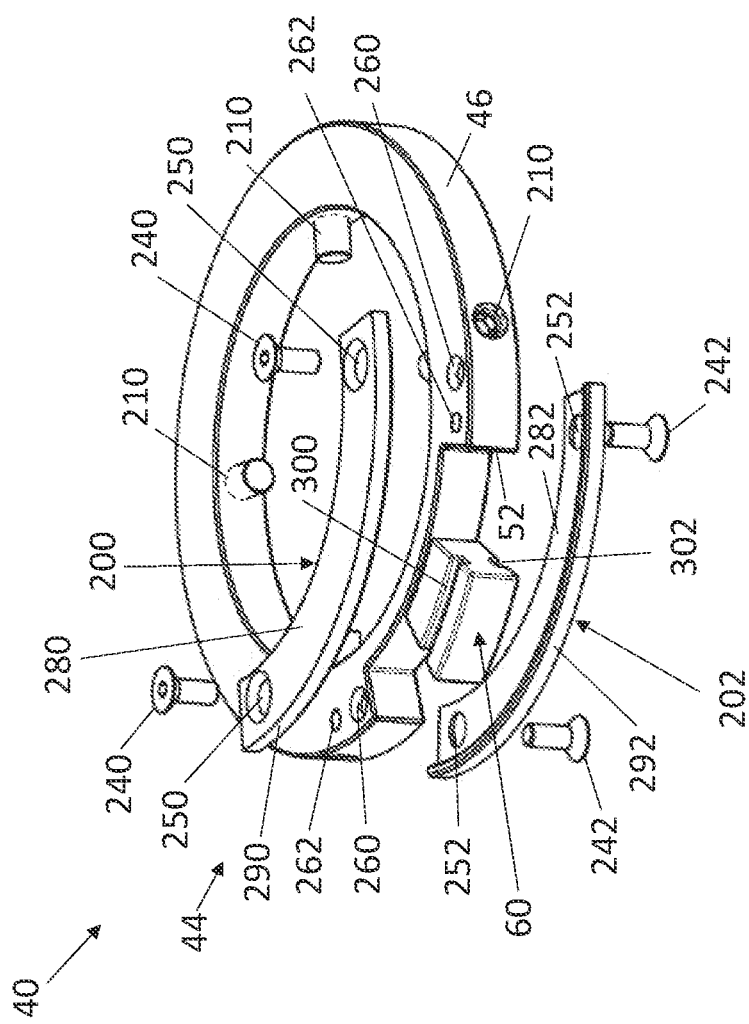
FIG. 11 is an exploded top isometric view of the rotational control mechanism, similar to the FIG. 7 view but showing the fasteners inserted in the rotation boundary member of the guide channel member.
Figure 12:
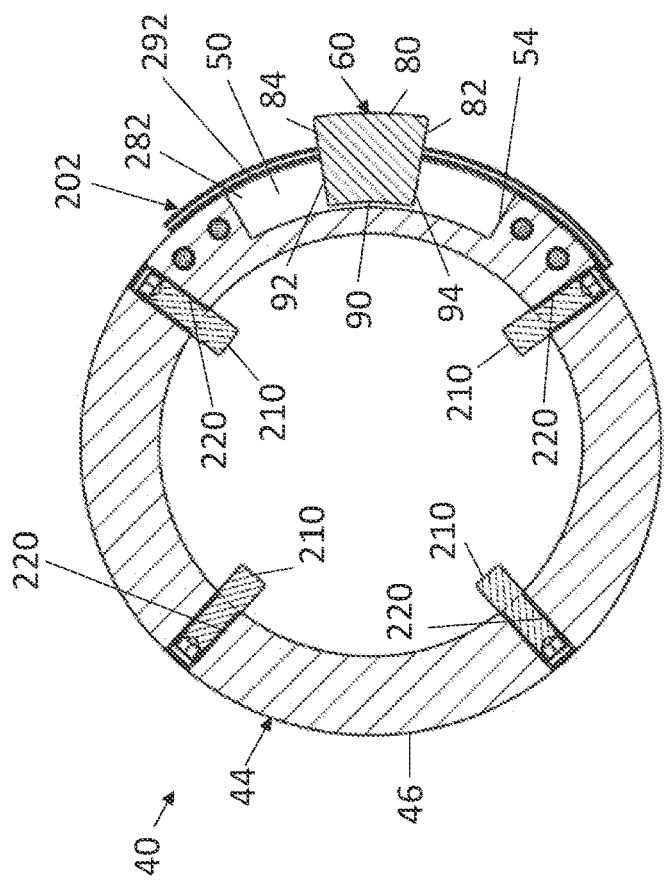
FIG. 12 is a top cross section view of the guide channel member and floating stop of the rotational control mechanism.

FIGS. 7 and 11-13 show greater detail of the guide channel member 44 and the floating stop 60 of the rotation control mechanism 40. The guide channel member 44 includes the rotation boundary member 46, an upper guide member 200, and a lower guide member 202. In the illustrative embodiment, the rotation boundary member 46 includes a ring shape structure wherein the inner diameter of the ring shape structure is slightly greater than the outer diameter of the shaft 14 to enable the rotation boundary member 46 to be slid axially onto the shaft 14 during assembly. The central axis of the ring shape structure coincides with the rotation axis A-A. The rotation boundary member 46 is fixed to the shaft 14 by four fasteners 210. In the illustrative embodiment, the fasteners 210 are socket set screws. The fasteners 210 are threaded into respective threaded openings 220 in the rotation boundary member 46 and into respective blind holes 230 in the shaft 14. In the illustrative embodiment, the centerlines of the fasteners 210, the threaded openings 220, and the blind holes 230 protrude radially from and perpendicular to the rotation axis A-A. When the fasteners 210 are tightened, the guide channel member 44 is fixed to the shaft 14 and, as shown in FIG. 12, the tops of the fasteners 210 are below the outer radius of the ring shape structure. As such, the tops of the fasteners 210 will not interfere with the fixed stop 70 during rotation of the extension arm 16 about the rotation axis A-A.

The fasteners 210 and the threaded openings 220 are positioned angularly outside of the arcuate span of the elongated cavity 50, and angularly outside of the upper and lower guide members 200, 202. It will be appreciated that the quantity and location of the fasteners 210 and the threaded openings 220 need not be limited as such, and other embodiments are contemplated. Any number of fasteners 210 may be used so long as the rotation boundary member 46 is securely fastened to the shaft 14. For example, three fasteners 210 and three threaded openings 220 may be used, where two are located adjacent to the respective opposite sides of the elongated cavity 50 and angularly outside of the upper and lower guide members 200, 202 and one is located diametrically opposite the angular center of the elongated cavity 50. In this case, the shaft 14 would have three blind holes 230 to accommodate the corresponding three fasteners 210. As another example, the fasteners 210, or even a single fastener 210, and a corresponding threaded opening or openings 220 in the rotation boundary member 46, may be located within the arcuate span of the elongated cavity 50, that is, between the opposite first and second contact faces 52, 54 of the elongated cavity 50. In this case, the threaded openings 220 may be in the arc shape wall of the cavity 50 for example. When the fasteners 210 are tightened, the guide channel member 44 is fixed to the shaft 14 and the tops of the fasteners 210 are below the outer radius of the arc shape wall such that the tops of the fasteners 210 will not interfere with the movement of the floating stop 60 within the elongated cavity 50 during rotation of the extension arm 16 about the rotation axis A-A.

In the illustrative embodiment, the rotation boundary member 46 includes a ring shape structure. Other shape structures may be suitable and are contemplated. For example, the rotation boundary member 46 may instead include an arc shape structure wherein the inner radius of the arc shape structure is slightly greater than the outer radius of the shaft 14 to enable the rotation boundary member 46 to be snugly fitted on the shaft 14 during assembly. Such arc shape structure would have an arcuate span sized to provide the elongated cavity 50 and the two fasteners 210 located adjacent to the respective opposite sides of the elongated cavity 50 and angularly outside of the upper and lower guide members 200, 202, in which case the shaft 14 would have two corresponding blind holes 230 to accommodate the two fasteners 210.

The upper guide member 200 and the lower guide member 202 are mounted to the rotation boundary member 46 by respective upper and lower fasteners 240, 242. In the illustrative embodiment, the fasteners 240, 242 are socket flat head cap screws. The upper fasteners 240 are inserted through through hole openings 250 in the upper guide member 200 and threaded into respective threaded openings 260 in the rotation boundary member 46. Similarly, the lower fasteners 242 are inserted through through hole openings 252 in the lower guide member 202 and threaded into respective threaded openings 262 in the rotation boundary member 46.

In the illustrative embodiment, the centerlines of the fasteners 240, 242, the through hole openings 250, 252, and the threaded openings 260, 262 extend axially and are parallel to the rotation axis A-A. When the upper fasteners 240 are tightened, the upper guide member 200 is secured to the rotation boundary member 46 and the tops of the flat heads of the upper fasteners 240 are substantially flush with or slightly below the upper surface of the upper guide member 200. Similarly, when the lower fasteners 242 are tightened, the lower guide member 202 is secured to the rotation boundary member 46 and the tops of the flat heads of the lower fasteners 242 are substantially flush with or slightly below the lower surface of the lower guide member 200. As will be appreciated, the upper and lower guide members 200, 202 add relatively little height to the guide channel member 44, thereby contributing to the rotational control mechanism 40 having a relatively smaller volumetric footprint than heretofore attained.

Figure 7:
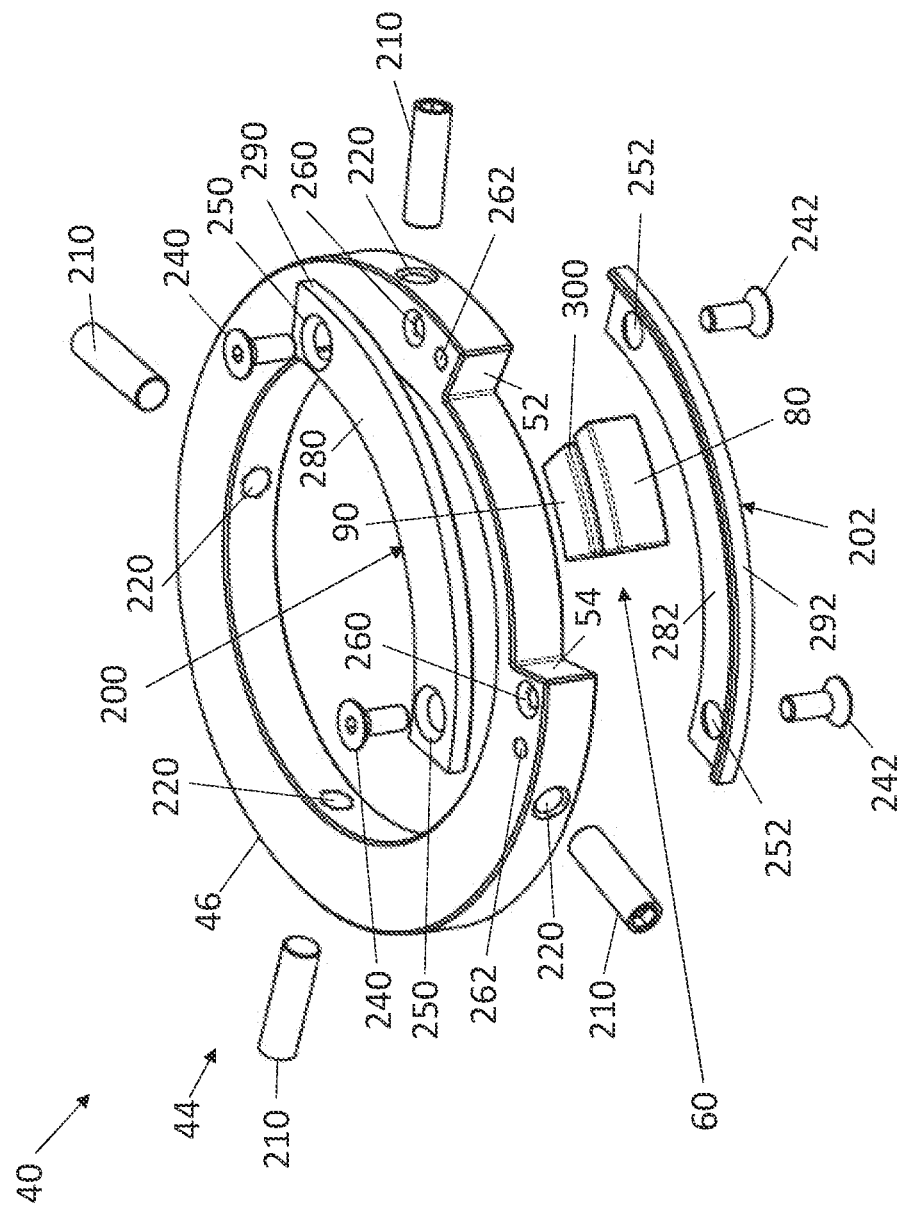
FIG. 7 is an exploded top isometric view of the rotational control mechanism, showing a guide channel member and a floating stop of the rotational control mechanism, the guide channel member including a rotation boundary member attached to the shaft and an elongated cavity that accommodates the floating stop.

As shown in FIGS. 7, 11 and 12, the fasteners 240, 242, the through hole openings 250, 252, and the threaded openings 260, 262 are positioned angularly outside of the arcuate span of the elongated cavity 50, and angularly inside of the fasteners 210 and threaded openings 220 used for securing the rotation boundary member 46 to the shaft 14. Also, in the illustrative embodiment, the upper and lower guide members 200, 202 have an identical geometry for economy of manufacture. As such, the upper guide member 200 and the upper fasteners 240 are staggered angularly relative to the lower guide member 202 and the lower fasteners 242, in the illustrative embodiment approximately 10° (10 degrees). As will be appreciated, the quantity and location of the fasteners 240, 242, the through hole openings 250, 252 and the threaded openings 260, 262 may be different from that illustrated, and other embodiments are contemplated. Any number of fasteners 240, 242 may be used so long as the upper and lower guide members 200, 202 are securely fastened to the rotation boundary member 46. For example, a single fastener may be used to secure the upper guide member 200 to the rotation boundary member 46, and a single fastener may be used to secure the lower guide member 202 to the rotation boundary member 46, where the guide members 200, 202 are provided with projections and/or recesses that engage respective recesses and/or projections in the rotation boundary member 46 to prevent movement therebetween. Also, the fasteners 240, 242, the through hole openings 250, 252, and the threaded openings 260, 262 may instead be positioned angularly outside of the fasteners 210 and the threaded openings 220 used for securing the rotation boundary member 46 to the shaft 14; in this way, the fasteners 210 and the threaded openings 220, as well as the blind holes 230 in the shaft 14, may be evenly spaced, i.e. equally angularly spaced, about the rotation axis A-A. It will further be appreciated that the upper and lower guide members 200, 202 may have different geometries and different corresponding locations for the through hole openings 250, 252 to accommodate the fasteners 240, 242.

Figure 13:
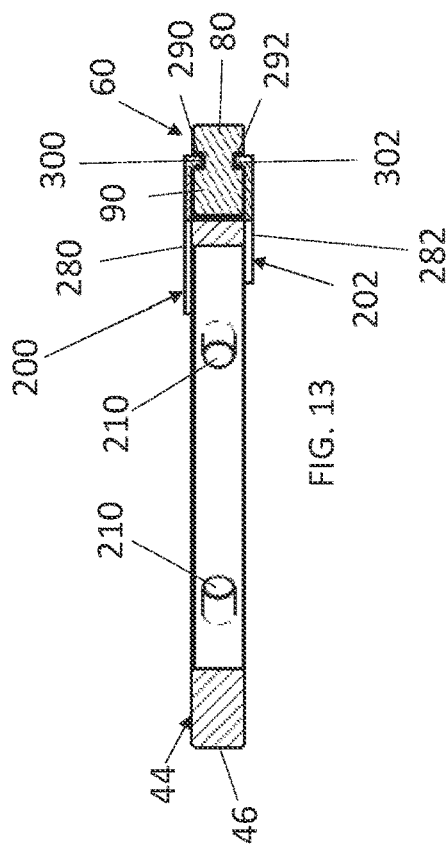
FIG. 13 is a side cross section view of the FIG. 12 rotational control mechanism.

The upper and lower guide members 200, 202 support, retain, and guide the floating stop 60. Referring to FIGS. 7 and 11, the upper guide member 200 includes an upper arc shape wall 280 and an upper arc shape track 290 projecting downwardly from the upper arc shape wall 280. The lower guide member 202 includes a lower arc shape wall 282 and a lower arc shape track 292 projecting upwardly from the lower arc shape wall 282. As shown in FIGS. 11 and 13, the floating stop 60 has an arc shape and includes upper and lower arc shape grooves 300, 302 in respective upper and lower surfaces of the floating stop 60. The floating stop 60 has an inner radius that is a first radial distance from the rotation axis A-A and an outer radius that is a second radial distance from the rotation axis A-A. The upper and lower arc shape grooves 300, 302 are located a radial distance from the rotation axis A-A that is greater than the first radial distance and less than the second radial distance. As shown in FIGS. 12 and 13, the upper and lower arc shape grooves 300, 302 are positioned at substantially the same radial distance from the rotation axis A-A as the respective upper and lower arc shape tracks 290, 292.

Together, the rotation boundary member 46, the upper and lower arc shape walls 280, 282 and the upper and lower arc shape tracks 290, 292 form the guide channel member 44 within which the floating stop 60 moves. The rotation boundary member 46 has an arc shape cut out that forms the elongated cavity 50, the opposite ends of the arc shape cut out providing the boundaries that form the first and second contact faces 52, 54 at opposite ends of the cavity 50. The arc shape cut out has an arc shape wall that is located a radial distance from the rotation axis A-A that is slightly less than the first radial distance that the inner radius of the floating stop 60 is located from the rotation axis A-A; this enables the inner radius of the floating stop 60 to slidably and/or freely move relative to the arc shape wall of the arc shape cut out during movement of the floating stop 60 within the elongated cavity 50 formed by the arc shape cut out. The upper and lower arc shape walls 280, 282 of the respective upper and lower guide members 200, 202 axially support the floating stop 60. The lower arc shape wall 282 axially supports the floating stop 60 to prevent axially downward movement of the floating stop 60 due to for example gravitational forces or incidental downward forces exhibited by the floating stop 60 during movement within the elongated cavity 50. The upper arc shape guide wall 280 axially supports the floating stop 60 to prevent axially upward movement of the floating stop 60 due to for example incidental upward forces exhibited by the floating stop 60 during movement within the elongated cavity 50. The upper and lower arc shape grooves 300, 302 of the floating stop 60 slidably receive the respective upper and lower arc shape tracks 290, 292 to radially retain the floating stop 60 and to angularly guide the floating stop 60 within the elongated cavity 50 and about the rotation axis A-A.

The floating stop 60 includes the afore described radially outer portion 80 and radially inner portion 90. In the illustrative embodiment, the radially outer portion 80 is located radially outward from the upper and lower arc shape tracks 290, 292 and the upper and lower arc shape grooves 300, 302. The radially inner portion 90 of the floating stop 60 is located radially inward from the upper and lower arc shape tracks 290, 292 and the upper and lower arc shape grooves 300, 302. As described above, the rotational control mechanism 40 can provide a greater than 360° (360 degrees) rotation range by adjusting the width (angular span) of the radially outer portion 80 of the floating stop 60, and/or the radially inner portion 90 of the floating stop 60. In one form, the angular span of the radially outer portion 80 of the floating stop 60, i.e. the portion of the floating stop 60 radially outward from the upper and lower arc shape tracks 290, 292 and the upper and lower arc shape grooves 300, 302, may be made relatively smaller than what is shown in the illustrative embodiment. In another form, the angular span of the radially inner portion 90 of the floating stop 60, i.e. the portion of the floating stop 60 radially inward from the upper and lower arc shape tracks 290, 292 and the upper and lower arc shape grooves 300, 302, may be made relatively smaller than what is shown in the illustrative embodiment.

As will be appreciated, in some embodiments the upper guide member 200 may be omitted, for example where upward forces exhibited by the floating stop 60 during movement within the elongated cavity 50 do not cause the floating stop 60 to shift and/or bind within the elongated cavity 50.

Referring now to FIGS. 8-10 and 12-13, the amount of radially inward protrusion of the radially inner portion 90 of the floating stop 60 relative to the outer radius of the guide channel member 44, or relative to the upper and lower arc shape tracks 290, 292, is such that the first and second contact faces 92, 94 of the radially inner portion 90 are at the same radial distance from the rotation axis A-A (or on the same circumference) as the first and second contact faces 52, 54 of the elongated cavity 50, and thus in operation abuttingly engage the respective first and second contact faces 52, 54.

FIGS. 3-5 and 8-10 show greater detail of the fixed stop 70 of the rotational control mechanism 40. In the illustrative embodiment, the fixed stop 70 is formed as part of the hub structure of the hub 34 and includes a block 70 with beveled edges forming the respective first and second contact faces 72, 74 on opposite peripheral sides of the block 70. The block 70, or fixed stop 70, protrudes axially downward from the hub structure that houses the brake assembly 160, which positions the fixed stop 70 and its first and second contact faces 72, 74 at the same axial location as the radially outer portion 80 of the floating stop 60 and its first and second contact faces 82, 84. As will be appreciated, the fixed stop 70 need not be formed as part of the hub structure of the hub 34 and may instead be a separate block that is attached to the hub structure.

Referring now to FIGS. 8-10, the amount of radially outward protrusion of the radially outer portion 80 of the floating stop 60 relative to the outer radius of the guide channel member 44, or relative to the upper and lower arc shape tracks 290, 292, is such that the first and second contact faces 82, 84 of the radially outer portion 80 are at the same radial distance from the rotation axis A-A (or on the same circumference) as the first and second contact faces 72, 74 of the fixed stop 70, and thus in operation abuttingly engage the respective first and second contact faces 72, 74.

Turning now to FIGS. 2-6 and 8-10, in the illustrative embodiment, the radially outer portion 80 of the floating stop 60 and the radially inner portion 90 of the floating stop 60 lie in the same plane and the plane is perpendicular to the rotation axis A-A. In this way, the rotational control mechanism 40 embodies fewer components and a smaller volumetric footprint than heretofore attained and simplifies and adds efficiency to the factory assembly and field service of the medical device support system 10. Also, the radially outer portion 80 of the floating stop 60 and the elongated cavity 50 of the guide channel member 44 lie in the same plane and the plane is perpendicular to the rotation axis A-A. Thus, in the embodiment of FIGS. 2-6 and 8-10, the radially outer portion 80, the radially inner portion 90, and the elongated cavity 50 lie in the same plane perpendicular to the rotation axis A-A. Of course, the invention need not be limited as such and other embodiments are contemplated. For example, the radially outer portion 80 may be located in a plane axially above or axially below the plane in which the radially inner portion 90 and the elongated cavity 50 lies. In another example, the radially outer portion 80 may be located in a plane axially above or axially below the plane in which the radially inner portion 90 lies, and the elongated cavity 50 may have an axial height such that the radially outer portion 80 and the radially inner portion 90, although themselves in different planes, both lie in the axial height plane of the elongated cavity 50.

In the illustrative embodiment, the fixed stop 70 of the hub 34 and the radially inner portion 90 of the floating stop 60 lie in the same plane and the plane is perpendicular to the rotation axis A-A. In this way, the rotational control mechanism 40 embodies fewer components and a smaller volumetric footprint than heretofore attained and simplifies and adds efficiency to the factory assembly and field service of the medical device support system 10. Also, the fixed stop 70 of the hub 34 and the elongated cavity 50 of the guide channel member 44 lie in the same plane and the plane is perpendicular to the rotation axis A-A. Thus, in the embodiment of FIGS. 2-6 and 8-10, the fixed stop 70, the radially inner portion 90, and the elongated cavity 50 lie in the same plane perpendicular to the rotation axis A-A. Of course, the invention need not be limited as such and other embodiments are contemplated. For example, the fixed stop 70 may be located in a plane axially above or axially below the plane in which the radially inner portion 90 and the elongated cavity 50 lies. In another example, the fixed stop 70 may be located in a plane axially above or axially below the plane in which the radially inner portion 90 lies, and the elongated cavity 50 may have an axial height such that the fixed stop 70 and the radially inner portion 90, although themselves in different planes, both lie in the axial height plane of the elongated cavity 50.

In the illustrative embodiment, the radially outer portion 80, the radially inner portion 90, the elongated cavity 50, and the fixed stop 70 all lie in the same plane perpendicular to the rotation axis A-A. In this way, the rotational control mechanism 40 embodies fewer components and a smaller volumetric footprint than heretofore attained and simplifies and adds efficiency to the factory assembly and field service of the medical device support system 10.

Figure 14:
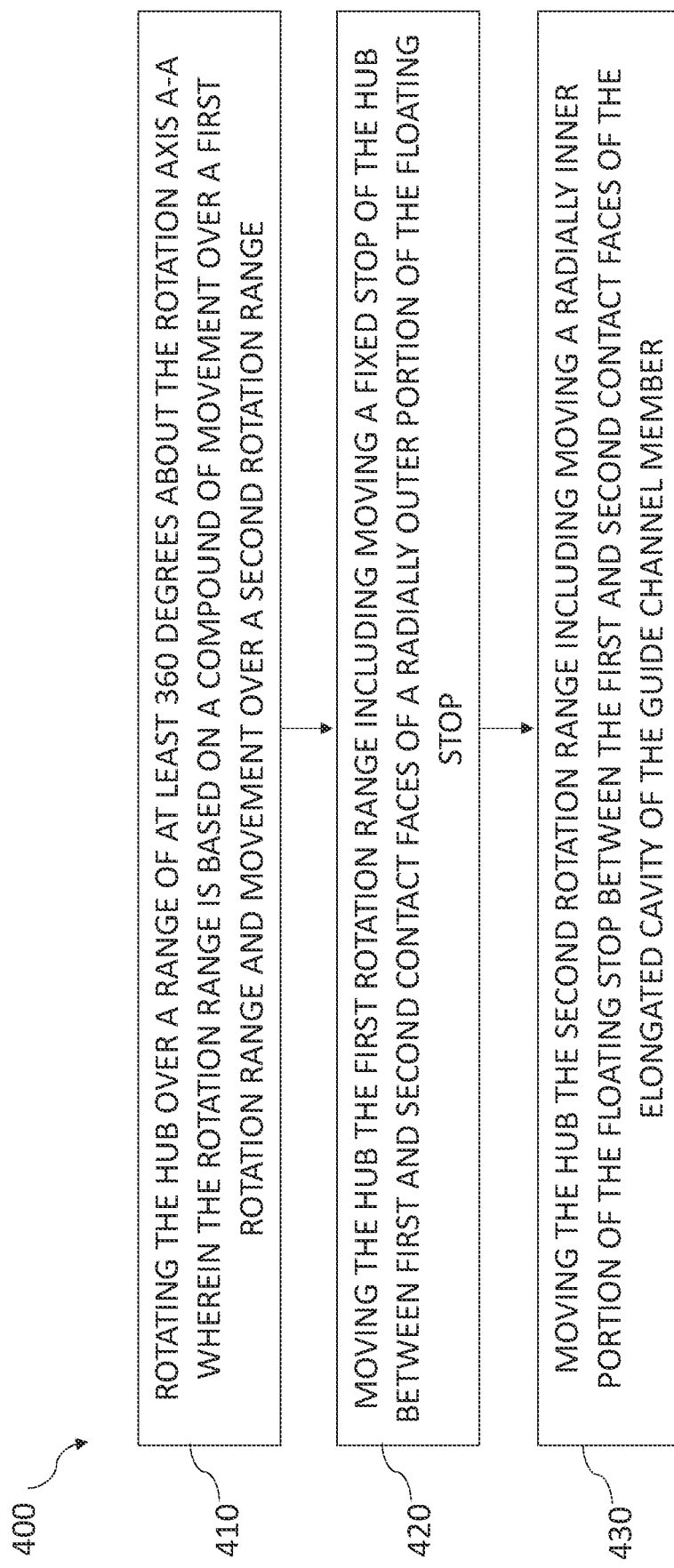
FIG. 14 shows a flowchart of a method of rotating an extension arm about a shaft of a medical device support system in accordance with an embodiment of the invention.

Referring now to FIG. 14, there is shown a flowchart 400 of a method of rotating an extension arm 16 about a shaft 14 of a medical device support system 10 such as shown in FIG. 1. The extension arm 16 has a support 20 for a medical device 30 and a hub 34 at its proximal end mounted to the shaft 14 for pivotable movement about a rotation axis A-A of the shaft 14. A guide channel member 44 is fixed to the shaft 14 and includes an elongated cavity 50 that defines first and second contact faces 52, 54 at opposite ends of the cavity 50. A floating stop 60 is movable within the elongated cavity 50 of the guide channel member 44 and movable relative to the hub 34. The method includes at step 410 rotating the hub 34 over a range of at least 360° (360 degrees) about the rotation axis A-A, wherein the at least 360° (360 degrees) rotation range is based on a compound of movement over a first rotation range and movement over a second rotation range. At step 420, the movement over the first rotation range includes moving a fixed stop 70 of the hub 34 between first and second contact faces 82, 84 of a radially outer portion 80 the floating stop 60. At step 430, the movement over the second rotation range includes moving a radially inner portion 90 of the floating stop 60 between the first and second contact faces 52, 54 of the elongated cavity 50 of the guide channel member 44.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system, comprising:
   a shaft;
   an extension arm having a support for a medical device and a hub at its proximal end mounted to the shaft for pivotable movement about a rotation axis of the shaft;
   a guide channel member that is fixed to the shaft;
   wherein the guide channel member includes an elongated cavity that defines first and second contact faces at opposite ends of the cavity;
   a floating stop movable within the elongated cavity of the guide channel member and movable relative to the hub;
   wherein the hub is pivotably mounted for a range of at least 360° (360 degrees) rotation about the rotation axis, wherein the at least 360° (360 degrees) rotation range is based on a compound of a first rotation range and a second rotation range, wherein the first rotation range is defined by a fixed stop of the hub configured to move between first and second contact faces of a radially outer portion of the floating stop, wherein the second rotation range is defined by a radially inner portion of the floating stop configured to move between the first and second contact faces of the elongated cavity of the guide channel member.

2. The medical device support system of claim 1, wherein the guide channel member includes a rotation boundary member that is fixed to the shaft, the rotation boundary member defining as boundaries the first and second contact faces at opposite ends of the cavity.

3. The medical device support system of claim 2, wherein the rotation boundary member includes a ring shape structure and the ring shape structure is fixed to the shaft.

4. The medical device support system of claim 1, wherein the elongated cavity has an arc shape.

5. The medical device support system of claim 1, wherein the guide channel member includes a lower guide wall for axially supporting the floating stop.

6. The medical device support system of claim 1, wherein the guide channel member includes an arc shape track and the floating stop includes an arc shape groove, wherein the arc shape groove slidably receives the arc shape track to angularly guide the floating stop within the elongated cavity and about the rotation axis.

7. The medical device support system of claim 1, wherein the floating stop is configured to prevent rotation of the hub about the rotation axis beyond the at least 360° (360 degrees) rotation range.

8. The medical device support system of claim 1, wherein the hub is pivotably mounted for at least 360° (360 degrees) rotation from a first stop to a second stop and vice versa, wherein the first stop limits counterclockwise rotation of the hub about the rotation axis and the second stop limits clockwise rotation of the hub about the rotation axis.

9. The medical device support system of claim 8, wherein the first stop includes the fixed stop of the hub in engagement with the first contact face of the radially outer portion of the floating stop, and the radially inner portion of the floating stop in engagement with the first contact face of the elongated cavity of the guide channel member.

10. The medical device support system of claim 8, wherein the second stop includes the fixed stop of the hub in engagement with the second contact face of the radially outer portion of the floating stop, and the radially inner portion of the floating stop in engagement with the second contact face of the elongated cavity of the guide channel member.

11. The medical device support system of claim 1, wherein the radially outer portion of the floating stop and the radially inner portion of the floating stop lie in the same plane and the plane is perpendicular to the rotation axis.

12. The medical device support system of claim 1, wherein the fixed stop of the hub and the radially inner portion of the floating stop lie in the same plane and the plane is perpendicular to the rotation axis.

13. The medical device support system of claim 1, wherein the radially outer portion of the floating stop includes a tab, and the first and second contact faces of the radially outer portion of the floating stop are on opposite peripheral sides of the tab.

14. The medical device support system of claim 1, wherein the radially inner portion of the floating stop has first and second contact faces on opposite sides thereof, and wherein the second rotation range is defined by movement of the radially inner portion between a location at which the first contact face of the radially inner portion engages the first contact face of the elongated cavity of the guide channel member and a location at which the second contact face of the radially inner portion engages the second contact face of the elongated cavity of the guide channel member.

15. The medical device support system of claim 3, wherein the shaft has an axial hollow and a radial aperture and wherein the ring shape structure is fixed to the shaft at a position to allow passage of electrical and communication lines through the axial hollow, through the ring shape structure, through the radial aperture, and into a longitudinally extending cavity in the extension arm.

16. The medical device support system of claim 15, wherein the hub of the extension arm includes upper and lower pivot bearings configured to pivotably engage the hub with the shaft, and a radial opening positioned axially between the upper and lower pivot bearings, and wherein the ring shape structure is positioned to allow passage of the electrical and communication lines between the upper and lower pivot bearings, through the radial opening of the hub, and into the longitudinally extending cavity in the extension arm.

17. A medical device support system, comprising:
a shaft;
an extension arm having a support for a medical device and a hub at its proximal end mounted to the shaft for pivotable movement about a rotation axis of the shaft;
a guide channel member that is fixed to the shaft;
wherein the guide channel member includes an elongated cavity that defines first and second contact faces at opposite ends of the cavity;
a floating stop movable within the elongated cavity of the guide channel member and movable relative to the hub;
wherein the hub is pivotably mounted for a range of at least 360° (360 degrees) rotation about the rotation axis from a first stop to a second stop and vice versa, wherein the first stop limits counterclockwise rotation of the hub about the rotation axis and the second stop limits clockwise rotation of the hub about the rotation axis,
wherein the first stop includes a radially inner portion of the floating stop in engagement with the first contact face of the elongated cavity of the guide channel member, and wherein the second stop includes the radially inner portion of the floating stop in engagement with the second contact face of the elongated cavity of the guide channel member.

18. The medical device support system of claim 17, wherein the hub includes a fixed stop movable between first and second contact faces of a radially outer portion of the floating stop.

19. The medical device support system of claim 18, wherein the first stop includes the fixed stop of the hub in engagement with the first contact face of the radially outer portion of the floating stop, and wherein the second stop includes the fixed stop of the hub in engagement with the second contact face of the radially outer portion of the floating stop.

20. A method of rotating an extension arm about a shaft of a medical device support system, the extension arm having a support for a medical device and a hub at its proximal end mounted to the shaft for pivotable movement about a rotation axis of the shaft, wherein a guide channel member is fixed to the shaft, wherein the guide channel member includes an elongated cavity that defines first and second contact faces at opposite ends of the cavity, wherein a floating stop is movable within the elongated cavity of the guide channel member and movable relative to the hub, the method comprising:
rotating the hub over a range of at least 360° (360 degrees) about the rotation axis, wherein the at least 360° (360 degrees) rotation range is based on a compound of movement over a first rotation range and movement over a second rotation range,
wherein movement over the first rotation range includes moving a fixed stop of the hub between first and second contact faces of a radially outer portion of the floating stop, and
wherein movement over the second rotation range includes moving a radially inner portion of the floating stop between the first and second contact faces of the elongated cavity of the guide channel member.

* * * * *